(12) United States Patent
Grashow et al.

(10) Patent No.: US 10,071,217 B2
(45) Date of Patent: Sep. 11, 2018

(54) GAS CARRYING HEADGEAR WITH POROUS BOUNDARY MEMBRANES

(71) Applicant: KONINKLIJKE PHILIPS N.V., Eindhoven (NL)

(72) Inventors: Jonathan Sayer Grashow, Pittsburgh, PA (US); Paul Denis McGroary, Gibsonia, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 785 days.

(21) Appl. No.: 14/394,836

(22) PCT Filed: Apr. 18, 2013

(86) PCT No.: PCT/IB2013/053078
§ 371 (c)(1),
(2) Date: Oct. 16, 2014

(87) PCT Pub. No.: WO2013/156960
PCT Pub. Date: Oct. 24, 2013

(65) Prior Publication Data
US 2015/0083136 A1   Mar. 26, 2015

Related U.S. Application Data

(60) Provisional application No. 61/636,222, filed on Apr. 20, 2012.

(51) Int. Cl.
*A61M 16/06* (2006.01)
*A61M 16/20* (2006.01)
(Continued)

(52) U.S. Cl.
CPC .... *A61M 16/0683* (2013.01); *A61M 16/0093* (2014.02); *A61M 16/06* (2013.01);
(Continued)

(58) Field of Classification Search
CPC .................................................. A61M 16/009
See application file for complete search history.

(56) References Cited

U.S. PATENT DOCUMENTS

| | | | |
|---|---|---|---|
| 4,558,708 A | 12/1985 | Labuda | |
| 5,826,573 A * | 10/1998 | Stegmann | A62B 9/00 128/200.24 |

(Continued)

FOREIGN PATENT DOCUMENTS

| | | |
|---|---|---|
| DE | 9411933 U1 | 10/1994 |
| DE | 19757703 C1 | 10/1999 |

(Continued)

*Primary Examiner* — Jackie Tan-Uyen T Ho
*Assistant Examiner* — Joseph D Boecker
(74) *Attorney, Agent, or Firm* — Michael W. Haas (57) ABSTRACT

A respiratory interface device is provided. The respiratory interface device includes at least one elongated support member structured to contact a user. The support member has at least one conduit portion and at least one porous portion. The conduit portion is structured to allow the passage of gas therethrough. The conduit portion is structured to be in fluid communication with a pressure generating system and with the porous portion. The porous portion is structured to allow for axial passage of gas therethrough and for radial exhaust of gas therefrom.

20 Claims, 7 Drawing Sheets

(51) Int. Cl.
*A61M 16/00* (2006.01)
*A61M 16/10* (2006.01)

(52) U.S. Cl.
CPC ...... *A61M 16/0611* (2014.02); *A61M 16/106* (2014.02); *A61M 16/107* (2014.02); *A61M 16/1065* (2014.02); *A61M 16/208* (2013.01); *A61M 2205/3331* (2013.01); *A61M 2205/7572* (2013.01); *A61M 2209/088* (2013.01)

(56) References Cited

U.S. PATENT DOCUMENTS

| | | | | |
|---|---|---|---|---|
| 8,353,293 | B1* | 1/2013 | Fuhrman | A61M 16/06 128/204.18 |
| 2003/0164170 | A1* | 9/2003 | Drew | A61M 16/06 128/204.18 |
| 2007/0095350 | A1* | 5/2007 | Darkin | A61M 16/06 128/206.24 |
| 2007/0246043 | A1* | 10/2007 | Kwok | A61M 16/0666 128/201.22 |
| 2008/0047560 | A1 | 2/2008 | Veliss et al. | |
| 2008/0060649 | A1 | 3/2008 | Veliss et al. | |
| 2009/0025724 | A1 | 1/2009 | Herron, Jr. | |
| 2009/0032024 | A1 | 2/2009 | Burz | |
| 2009/0044808 | A1* | 2/2009 | Guney | A61M 16/0666 128/206.24 |
| 2009/0044810 | A1 | 2/2009 | Kwok | |
| 2009/0050156 | A1* | 2/2009 | Ng | A61M 16/06 128/205.24 |
| 2009/0139528 | A1* | 6/2009 | Yevich | A61M 16/047 128/207.14 |
| 2009/0272380 | A1 | 11/2009 | Jaffre | |
| 2010/0154798 | A1* | 6/2010 | Henry | A61M 16/06 128/206.24 |
| 2010/0170514 | A1 | 7/2010 | Omer-Cooper | |
| 2010/0224195 | A1 | 9/2010 | Henry | |
| 2011/0232646 | A1 | 9/2011 | Ho | |
| 2014/0137870 | A1* | 5/2014 | Barlow | A61M 16/0057 128/205.25 |
| 2014/0283831 | A1* | 9/2014 | Foote | A61M 16/009 128/204.19 |
| 2016/0008566 | A1* | 1/2016 | Partington | A61M 16/06 128/201.13 |

FOREIGN PATENT DOCUMENTS

| | | |
|---|---|---|
| EP | 0697225 A2 | 2/1996 |
| EP | 2027880 A1 | 2/2009 |
| GB | 2241896 A1 | 9/1991 |
| WO | WO2009149507 A1 | 12/2009 |

* cited by examiner

GAS CARRYING HEADGEAR WITH POROUS BOUNDARY MEMBRANES

CROSS-REFERENCE TO RELATED APPLICATIONS

This patent application claims the claims the priority benefit under 35 U.S.C. § 371 of international patent application no. PCT/IB2013/053078, file Apr. 18, 2013, which claims the priority benefit under 35 U.S.C. § 119(e) of U.S. Provisional Application No. 61/636,222 filed on Apr. 20, 2012, the contents of which are herein incorporated by reference.

BACKGROUND OF THE INVENTION

1. Field of the Invention

The present invention relates to respiratory interface devices for transporting a gas to and/or from an airway of a user which include, but are not limited to, a mask having a flexible faceplate or patient contacting cushion, and, in particular, to a flexible respiratory interface device wherein the support assembly is structured to allow gas to pass therethrough including a flow as a radial exhaust.

2. Description of the Related Art

A variety of respiratory masks are known which cover the areas surrounding the nose and/or mouth of a human user. Typically, gases can be provided at a positive pressure within the mask for consumption by the user. The uses for such masks include high altitude breathing (aviation applications), swimming, mining, fire-fighting, and various medical diagnostic and therapeutic applications. The masks are, typically, held in place by a support assembly having one or more straps.

Support assemblies may include a plurality of straps disposed in various configurations depending upon the mask and the user's preference. Generally, however, the support assembly includes at least one strap that extends about a user's head while having the two ends coupled to the mask disposed on the user's face. Additional straps may position the primary strap in a comfortable location, and/or may assist in positioning and maintaining the mask in the proper location. Thus, at least one strap extends over the user's face and, more typically, over the user's cheeks.

Straps may be made from various materials such as, but not limited to, fabric, plastic, or silicone. In some embodiments, the straps define, or enclose, a conduit that is in fluid communication with the mask, which may eliminate the need for a separate conduit coupled directly to the mask. The conduit may also be in fluid communication with a device capable of generating a flow of breathing gas or providing gas at an elevated pressure. The straps, even straps made from a breathable material, may become uncomfortable over a period of time. That is, the straps tend to remain positioned over the same area of the user's face and may trap heat and sweat thereunder. This is especially true when the strap encloses a conduit as such straps do not breath.

Further, certain types of masks include an exhaust port structured to allow expired gases to be vented to the atmosphere. The expired gases may "jet" from the exhaust port in a concentrated stream. This stream may cross the user's face, or may be directed to an adjacent space; such as the space occupied by people in close proximity to the user, e.g. a bed partner. Thus, the exhaust stream may be uncomfortable for either the user, another person, or both.

Accordingly, there is a need for a support assembly that allows for airflow under at least portions of the strap assembly. There is a further need for a support assembly that assists in dissipating an exhaust jet from a mask.

SUMMARY OF THE INVENTION

One embodiment of the present invention provides a respiratory interface device including at least one elongated support member structured to contact a user, the at least one support member having at least one conduit portion and at least one porous portion. The conduit portion is structured to allow the passage of gas therethrough. The conduit portion is structured to be in fluid communication with a pressure generating system and in fluid communication with the porous portion. The porous portion is structured to allow for axial passage of gas therethrough and to allow for radial exhaust of gas therefrom to the ambient environment. The porous portion is in fluid communication with the mask.

It is an object of this invention to provide a method of using the respiratory interface device by performing the steps of: positioning mask over at least one of the user's nose or mouth, generating a flow of pressurized gas, communicating the pressurized gas via support assembly to mask, and exhausting a portion of the pressurized gas radially through support member at least one porous portion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As used herein, elements "in fluid communication" means that a passage capable of allowing a fluid to pass therethrough extends between the elements.

As used herein, "rigid" means substantially unbendable. As used herein, "stiff" means structured to maintain a shape when unbiased, but bendable when exposed to a minimal bias. For example, a thin wire, such as but not limited to, a wire used in a twist tie, may be easily bent but will thereafter maintain its configuration until bent again. As used herein, a "shape maintaining member" is a member that is flexible when exposed to a bias, but returns to its original configuration when the bias is removed; such as, but not limited to, a semi-hard plastic. As used herein, a "tension member" is a construct that has a maximum length when exposed to tension, but is otherwise substantially flexible, such as, but not limited to, a chain.

As used herein, a "porous" material allows gas to pass therethrough, but not as a jet, i.e. a discrete stream. That is, a "porous" material allows gas to dissipate therethrough.

Figure 1:
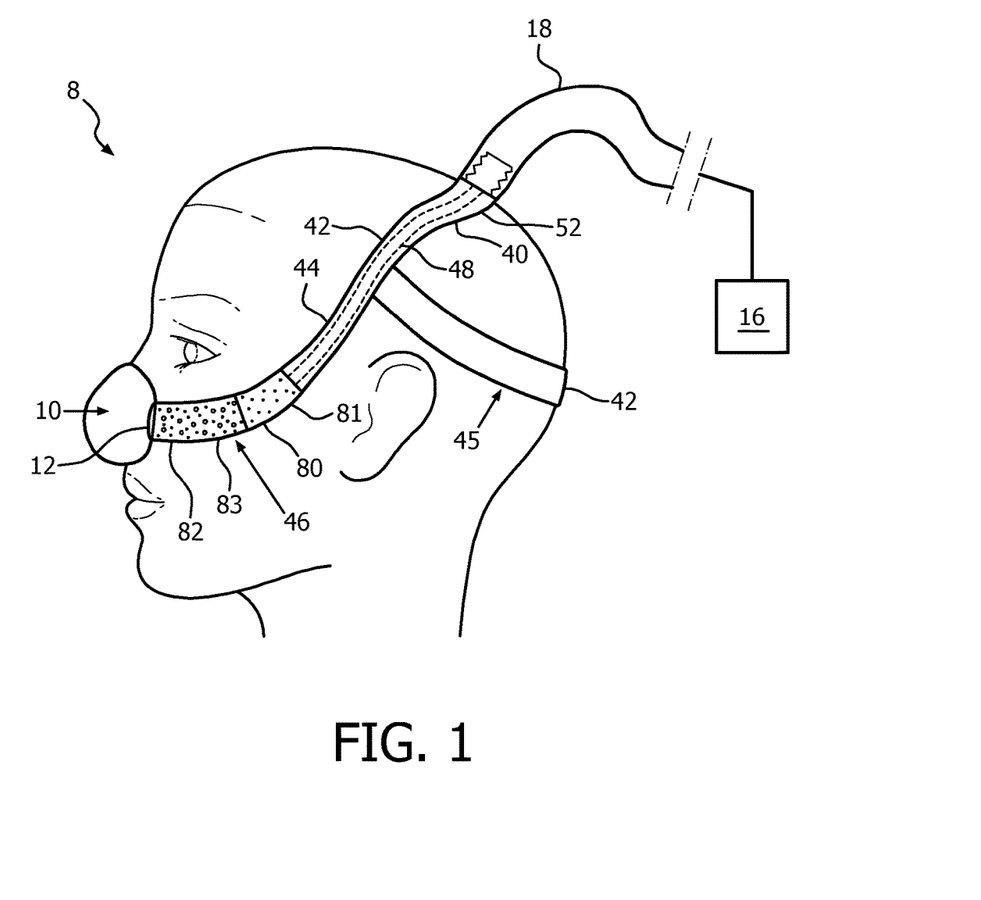
FIG. 1 is an isometric view of a respiratory interface device.

As shown in FIG. 1, a respiratory interface device 8 includes a respiratory mask 10 (shown schematically) and a support assembly 40. Mask 10 includes an opening 12 defining a passage therethrough. That is, as used herein, mask "opening" 12 allows for gas to pass to the enclosed space between mask 10 and the user so that the user may breath the gas. Mask 10 is coupled to a pressure generating system 16 (shown schematically) via a patient circuit, as is conventionally known in the art. That is, pressure generating system 16 is coupled to, and in fluid communication with, respiratory interface device 8 via a hose 18 or similar construct. For purposes of the present invention, pressure generating system 16 is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV) device, proportional positive airway pressure (PPAP) device, C-Flex™ device, Bi-Flex™ device, or a BiPAP™ device manufactured and distributed by Philips Respironics of Murrysville, Pa., in which the pressure provided to the patient varies with the patient's respiratory cycle so that a higher pressure is delivered during inspiration than during expiration, or other pressure support device. Pressure generating system 16 is in fluid communication with the interior side of mask 10 via mask opening 12.

As shown, mask 10 is structured to cover the nose of the user. It is understood that this is an exemplary embodiment and that support assembly 40 could be used with any type of mask, such as, but not limited to, an oral and nasal mask. Thus, mask 10 is structured to provide a gas to at least one of the user's nose or mouth. It is further understood that support assembly 40, as shown, is configured to be coupled to the disclosed mask 10 and that other masks may use support assemblies 40 having different configurations. That is, as shown, support assembly 40 is disposed about the user's head. It is understood that support assembly 40 may also extend, or have elements that extend, about the user's neck, arm, or other body parts. Thus, it is understood that the disclosed invention is not limited to the embodiments as shown.

Support assembly 40 includes at least one elongated support member 42, commonly identified as a strap. At least one elongated support member 42 is structured to directly contact a user. That is, when in use, at least one elongated support member 42 rests upon a portion of the user's head. As shown in FIG. 1 there are two support members 42. At least one elongated support member 42 may include at least one conduit portion 44 and at least one porous portion 46. The other support member is a strap 45. Support member at least one conduit portion 44 and support member at least one porous portion 46 are coupled to, and in fluid communication with, each other.

Support member at least one conduit portion 44 is structured to allow the passage of gas therethrough. That is, support member at least one conduit portion 44 defines a passage 48. Support member at least one conduit portion 44 may be substantially separate from at least one elongated support member 42. In one exemplary embodiment (not shown) support member at least one conduit portion 44 is a tube directly coupled to, and in fluid communication with, support member at least one porous portion 46, but otherwise not coupled to at least one elongated support member 42. That is, as used herein, support member at least one conduit portion 44 may have minimal, or no, direct contact with at least one elongated support member 42 and is still be part of support assembly 40. In another exemplary embodiment, support member at least one conduit portion 44 is made from a non-porous membrane 52 that defines passage 48. In another exemplary embodiment (not shown), support member at least one conduit portion 44 includes a porous member 43, such as but not limited to fabric, that encloses a non-porous conduit such as, but not limited to, a plastic tube. Support member at least one conduit portion 44 is further structured to be in fluid communication with pressure generating system 16. Thus, support member at least one conduit portion 44 is structured to allow for the axial flow of gas therethrough.

Support member at least one porous portion 46 is structured to allow for axial passage of gas therethrough and radial exhaust of gas therethrough. Support member at least one porous portion 46 is a porous body 50 from a material selected from the group including cell foam, woven material, fibrous textile, a material having micro-passages, i.e. passages with a radius of about 0.5 mm or less or a combination of any of these materials. In an exemplary embodiment, support member at least one porous portion 46 defines a primary passage assembly 60 (FIGS. 2 and 3) structured to provide a conduit for the axial passage of gas. In an exemplary embodiment, FIG. 2, primary passage assembly 60 is a longitudinally extending single passage 62. In another exemplary embodiment, FIG. 3, primary passage assembly 60 is a plurality of longitudinally extending passages 70. In an exemplary embodiment shown in FIG. 4, primary passage assembly single passage 62 has a reducing radius. That is, for example, single passage 62 may have a circular cross-section. At an upstream location 64 of single passage 62, single passage 62 has a greater radius, and, at a downstream location 66 of single passage 62, single passage 62 has a lesser radius. The change from the greater radius to a lesser radius may occur gradually, i.e. tapered over the length of single passage 62 (not shown), in one or more discrete steps, i.e. at a perpendicular, inwardly extending flange (not shown), or in one or more tapered steps, as shown in FIG. 4. In an embodiment having a plurality of longitudinally extending passages 70, selected passages 70A may terminate at a lesser longitudinal length than other selected passages 70B. Thus, the overall cross-sectional area of primary passage assembly 60 is reduced at the point where selected passages 70A terminate.

By selecting a specific cross-sectional area for primary passage assembly 60, or by altering the cross-sectional area for primary passage assembly 60, support member at least one porous portion 46 is structured to have a selected axial flow rate. That is, the axial flow rate may be substantially constant, i.e. the cross-sectional area of primary passage assembly 60 may remain substantially constant, or, the axial flow rate may be variable, i.e. the cross-sectional area of primary passage assembly 60 may vary.

Support member at least one porous portion 46 is further structured to allow for at least one radial exhaust rate. That is, support member at least one porous portion 46 allows for gas to escape radially. As used herein, "radially" is to be interpreted broadly and in reference to the local longitudinal axis of at least one elongated support member 42. It is noted that the gas may leave the outer surface of support member at least one porous portion 46 at a random direction. That is, support member at least one porous portion 46 is porous and allows gas to pass therethrough. Thus, support member at least one porous portion 46 has at least one radial exhaust rate. The at least one radial exhaust rate may be controlled by providing porous materials with differing degrees of porosity, as discussed below, or by altering the cross-sectional area of primary passage assembly 60 and thereby altering the fluid pressure within support member at least one porous portion 46.

For example, as shown in FIG. 1, support member at least one porous portion 46 may include at least a first section 80 and a second section 82. Support member at least one porous portion first section 80 has a first radial exhaust rate, and, support member at least one porous portion second section 82 has a second radial exhaust rate. Support member at least one porous portion first section 80 and support member at least one porous portion second section 82 may be disposed in series or extend coextensively along support member at least one porous portion 46.

That is, when support member at least one porous portion first section 80 and support member at least one porous portion second section 82 are disposed in series, as shown in FIG. 1, the support member at least one porous portion first section 80 is a first body 81 made from a first porous material having a first radial exhaust rate. Thus, gas may escape in any direction through support member at least one porous portion first section 80. The support member at least one porous portion second section 82 is a second body 83 made from a second porous material having a second radial exhaust rate. Support member at least one porous portion first section 80 and support member at least one porous portion second section 82 are coupled and in fluid communication. For example, at least one porous portion first section 80 may be disposed adjacent the user's ears and allow for a minimal radial flow rate as the escaping gas may create a noise and the noise level should be minimal. Support member at least one porous portion second section 82 may be disposed over the user's cheek and allow for a greater radial flow rate so as to help cool the user's face. It is further noted that to be disposed in series, first body 81 and second body 83 may be directly coupled or may be separated by a support member at least one conduit portion 44, so long as first body 81 and second body 83 are in fluid communication.

Figure 5:
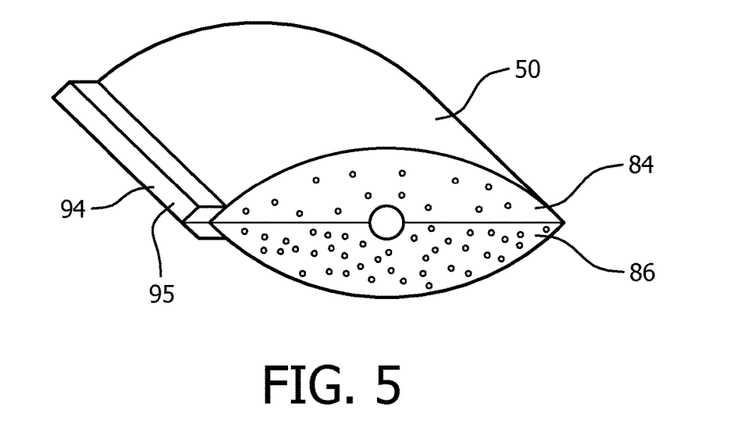
FIG. 5 is a cross-sectional view of another embodiment of the support member at least one porous portion.

In another exemplary embodiment, shown in FIG. 5, support member at least one porous portion first section 80 and support member at least one porous portion second section 82 may extend coextensively along support member at least one porous portion 46. That is, first area, such as, but not limited to, a first side 84 of support member at least one porous portion 46 may be made from a first porous material having a first radial exhaust rate, and a second area, such as, but not limited to, a second side 86 of support member at least one porous portion 46 may be made from a second porous material having a second radial exhaust rate. Thus, the two opposing sides 84, 86 of support member at least one porous portion 46 have different exhaust rates. Thus, a user could place one of at least one porous portion first section 80 or support member at least one porous portion second section 82 against the user's face depending upon the flow rate desired. For example, on a hot day the user may select one of at least one porous portion first section 80 or support member at least one porous portion second section 82 having a greater flow rate, thereby increasing the cooling effect of the radial exhaust. Conversely, on a cool day the user may reverse the radial orientation of support member at least one porous portion 46 thereby placing the other at least one porous portion first section 80 or support member at least one porous portion second section 82 against the user's face, thereby minimizing the cooling effect of the radial exhaust.

Alternatively, the radial exhaust rate may be controlled by altering the pressure of the gas in primary passage assembly 60. That is, pressure generating system 16 provides gas at a selected pressure via fluid communication to support member at least one porous portion 46 and more specifically to primary passage assembly 60. Gas following in primary passage assembly 60 is under pressure and that pressure causes some of the gas to move radially through support member at least one porous portion 46. If the cross-sectional area of primary passage assembly 60 decreases, as described above, the pressure in primary passage assembly 60 increases. When the pressure in primary passage assembly 60 increases, a greater amount of the gas moves radially through support member at least one porous portion 46. Thus, the radial exhaust rate may be controlled by altering the cross-sectional area of the primary passage assembly 60 which, in turn, alters the pressure of the gas in primary passage assembly 60.

Figure 6A:
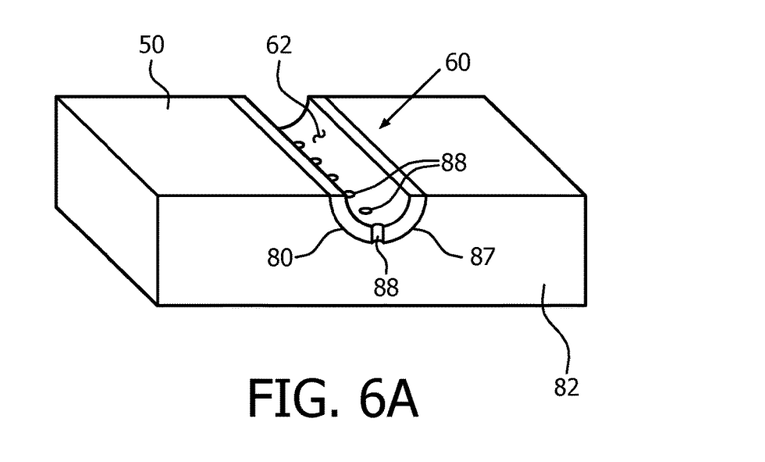
FIG. 6A is a cross-sectional view of another embodiment of the support member at least one porous portion.
Figure 6B:
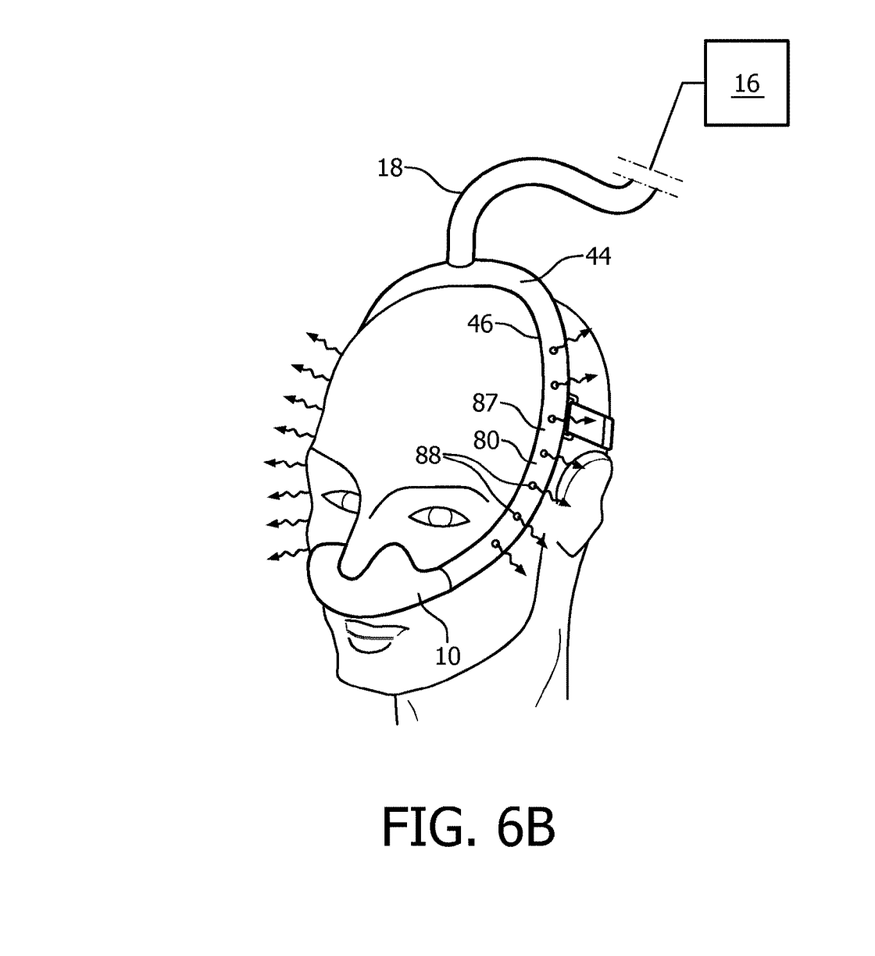
FIG. 6B is a partial isometric view of the respiratory interface device using the support member at least one porous portion of FIG. 6A.
Figure 6C:
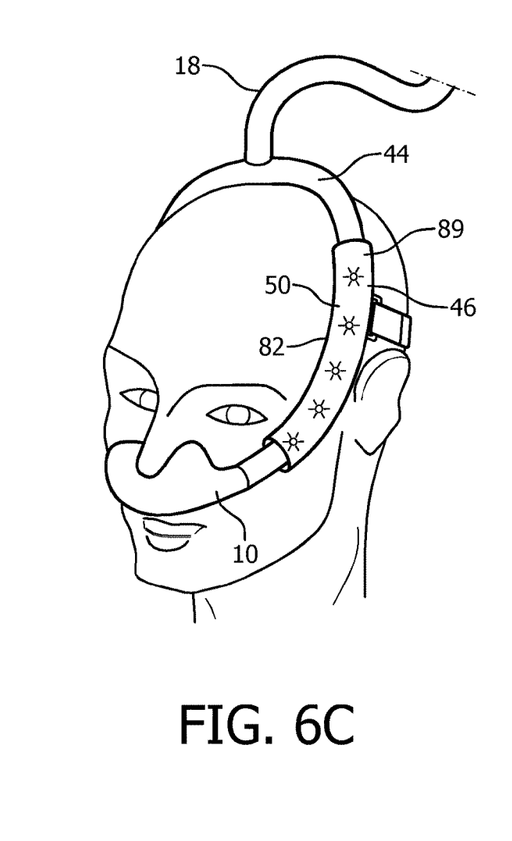
FIG. 6C is an isometric view of the respiratory interface device using the support member at least one porous portion of FIG. 6A.

In another exemplary embodiment, shown in FIG. 6A-6C, and when support member at least one porous portion first section 80 and support member at least one porous portion second section 82 extend coextensively along support member at least one porous portion 46, at least one porous portion first section 80 may be substantially enclosed within support member at least one porous portion second section 82. At least one porous portion first section 80 is a tubular conduit 87, such as, but not limited to a silicone tube, having a plurality of radial openings 88. At least one porous portion first section 80 is disposed within a porous body 50, such as but not limited to a porous fabric cover 89, that forms support member at least one porous portion second section 82. As shown in FIG. 6B, support member at least one porous portion first section 80 is coupled to, and in fluid communication with, pressure generating system 16 (shown schematically) via support member at least one conduit portion 44. It is noted that openings 88 are shown as being visible, but, in an exemplary embodiment, are micro-openings; thus tubular conduit 87 is a porous body 50 and at least one porous portion first section 80. As shown in FIG. 6C, at least one porous portion first section 80 may be further substantially enclosed in support member at least one porous portion second section 82, which is shown as fabric cover 89.

It is further noted that support member at least one porous portion 46 may not be divided into two sections 80, 82 in that openings 88 may not be micro-openings; thus tubular conduit 87 would not meet the definition of a porous body 50 required for a support member at least one porous portion 46. In this exemplary embodiment, support member at least one porous portion 46 includes a tubular conduit 87 having radial openings 88 that are larger than micro-openings and a fabric cover 89. When fabric cover 89 is disposed over tubular conduit 87, support member at least one porous portion 46 is created. Support member at least one porous portion tubular conduit 87 is substantially enclosed within support member at least one porous portion fabric cover 89. Thus, if larger openings are used, the porous fabric cover is the porous body 50 that creates the support member at least one porous portion 46.

Figure 7:
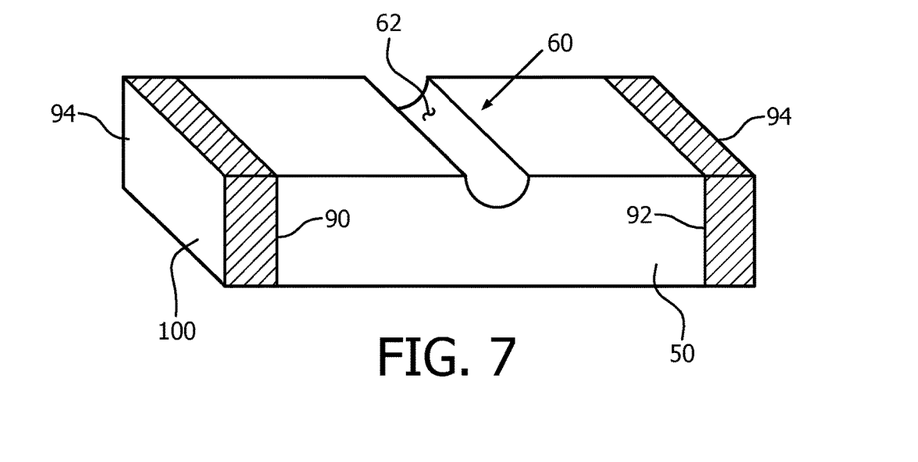
FIG. 7 is a cross-sectional view of another embodiment of the support member at least one porous portion.

It is further noted that support member at least one porous portion 46 may include a non-porous layer. In an exemplary embodiment, shown in FIG. 7, support member at least one porous portion 46 has a rectangular cross-sectional shape. In this configuration, support member at least one porous portion 46 has two lateral sides 90, 92. Lateral sides 90, 92 may further include a less porous, e.g. a densely woven fabric, or non-porous, e.g. plastic, layer 94. As used herein, "non-porous layer 94" shall include a substantially non-porous layer. In this configuration, one of support member at least one porous portion 46 non-lateral sides is disposed against the user's face. Thus, gas being radially exhausted is directed either toward the user's face, away from the user's face, or both. That is, the gas cannot pass through non-porous layer 94 and parallel to the user's face.

It is further noted that non-porous layer 94 may be made from a material that is stronger than a foam or other materials that may be used to create the porous portions of support member at least one porous portion 46. Thus, non-porous layer 94 may act as a type of reinforcement assembly 100 that protects the porous portions of support member at least one porous portion 46. In an exemplary embodiment, shown in FIG. 8, non-porous layer 94 is external to support member at least one porous portion 46 and acts as a partial shell 95 disposed on the periphery, and more specifically, on the lateral sides of support member at least one porous portion 46. In another exemplary embodiment, non-porous layer 94 may extend over a more substantial portion of the outer surface of support member at least one porous portion 46. For example, and using the rectangular cross-section configuration described above, non-porous layer 94 may extend over support member at least one porous portion lateral sides 90, 92 as well as outer non-lateral side 96. In this configuration, the radially exhausting gas will be substantially directed toward the user's face.

Figure 3:
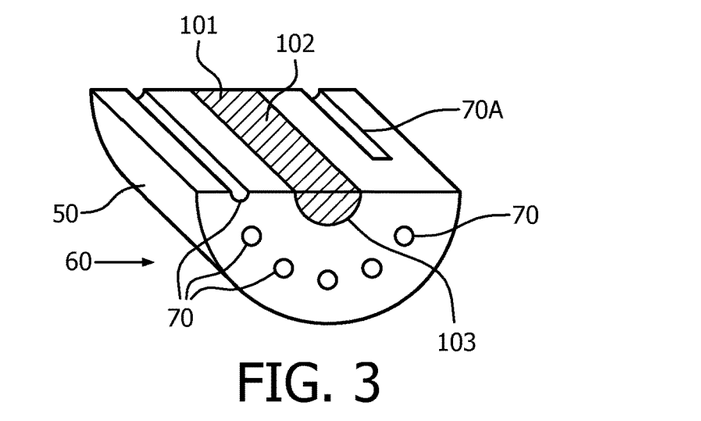
FIG. 3 is a cross-sectional view of another embodiment of the support member at least one porous portion.
Figure 4:
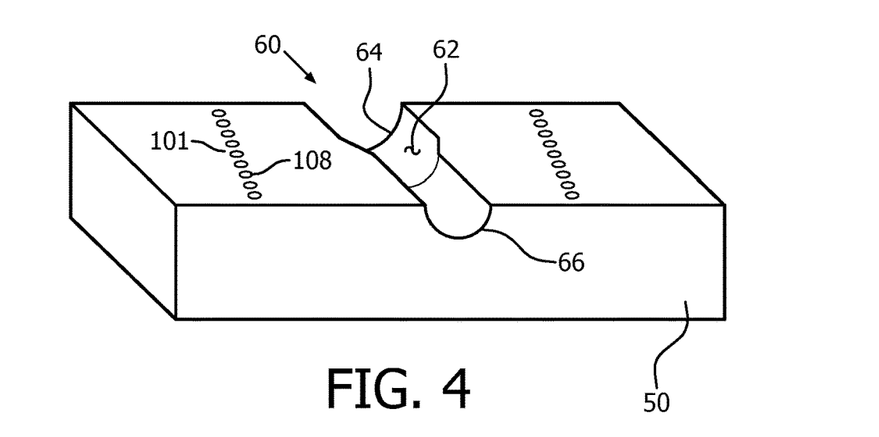
FIG. 4 is a cross-sectional view of another embodiment of the support member at least one porous portion.
Figure 9:
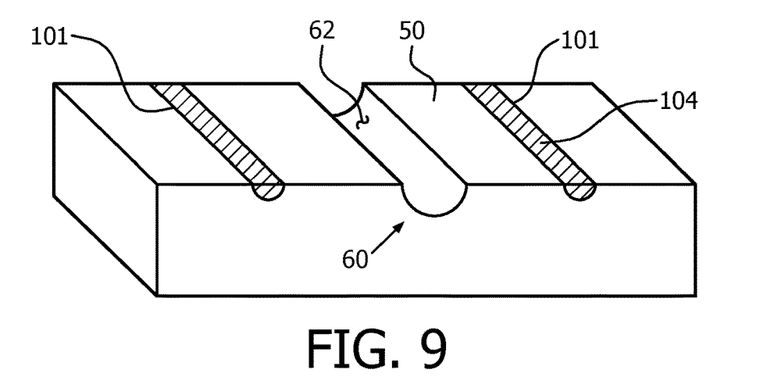
FIG. 9 is a cross-sectional view of another embodiment of the support member at least one porous portion.

Reinforcement assembly 100 may include other types of reinforcing elements, notably internal elements 101 (FIGS. 3 and 9). For example, support member at least one porous portion 46 includes at least one reinforcing element 101 selected from the group including a rigid member 102 (FIG. 3), a stiff member 104 (FIG. 9), a shape maintaining member 106 (FIG. 10) and a tension member 108 (FIG. 4). Rigid member 102 may be used when it is desirable to define a specific shape for support member at least one porous portion 46. For example, rigid member 102 may be disposed within support member at least one porous portion 46, such as but not limited to, a steel rod 103 (FIG. 3) about which a plurality of longitudinally extending passages 70 are formed, or, a plurality of rigid members 102 may be disposed about single passage 62, similar to what is shown in FIG. 9. Further, rigid members 102 may be disposed in serial, i.e. rigid members 102 may be coupled at a movable coupling such as, but not limited to a spherical bearing (not shown) or simply disposed adjacent to each other without a coupling. In such an exemplary embodiment, selected portions of support member at least one porous portion 46 will be rigid while being movable relative to each other.

As with rigid member 102, stiff members 104 may be disposed in a central location with a plurality of longitudinally extending passages 70 disposed thereabout, or, a plurality of stiff members 104 may be disposed about single passage 62, as shown in FIG. 9. Stiff members 104 may be used if it is desirable to allow the user to shape support member at least one porous portion 46 in a desired configuration. For example, if in an original configuration, support member at least one porous portion 46 is positioned over the corner of the user's mouth, the user may bend support member at least one porous portion 46 having stiff members 104 so as to avoid this area.

Figure 8:
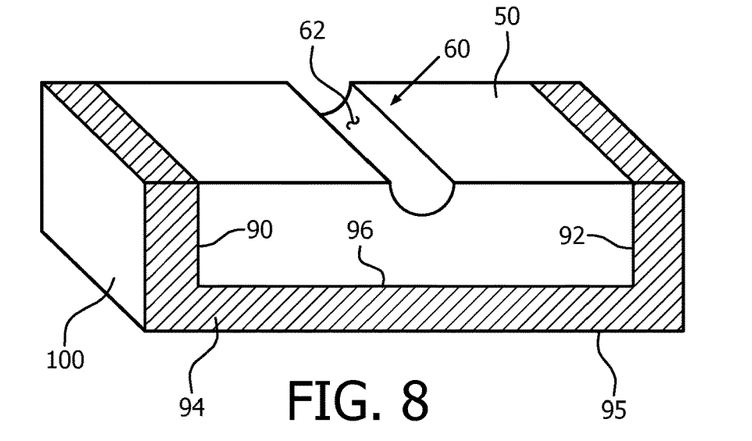
FIG. 8 is a cross-sectional view of another embodiment of the support member at least one porous portion.
Figure 10:
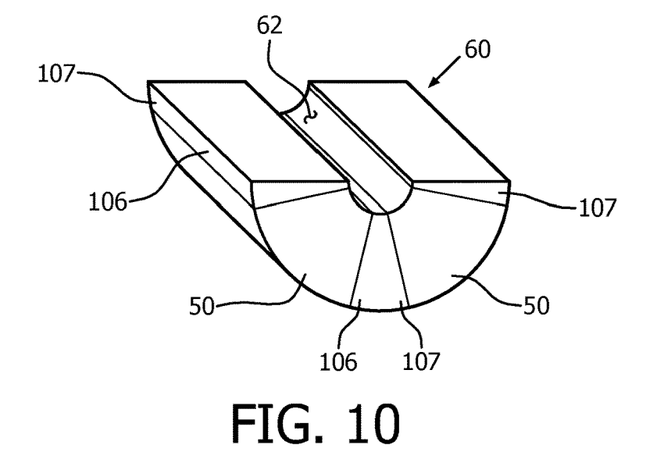
FIG. 10 is a cross-sectional view of another embodiment of the support member at least one porous portion

Shape maintaining member 106, FIG. 10, may be used when a rigid member 102 is too inflexible, but it is desirable for support member at least one porous portion 46 to maintain its shape. Shape maintaining member 106 may be, but is not limited to, at least one longitudinally extending rib 107. Tension member 108 (FIG. 4)) may be used when support member at least one porous portion 46 is intended to be flexible, but is made from a weak material that may be accidentally pulled apart. Thus, support member at least one porous portion 46 may include at least one reinforcing internal element 101 selected from the group including a rigid member 102 (FIG. 3), a stiff member 104 (FIG. 9), a shape maintaining member 106 (FIG. 10) a tension member 108 (FIG. 4), and a partial shell 95 (FIG. 8).

Figure 2:
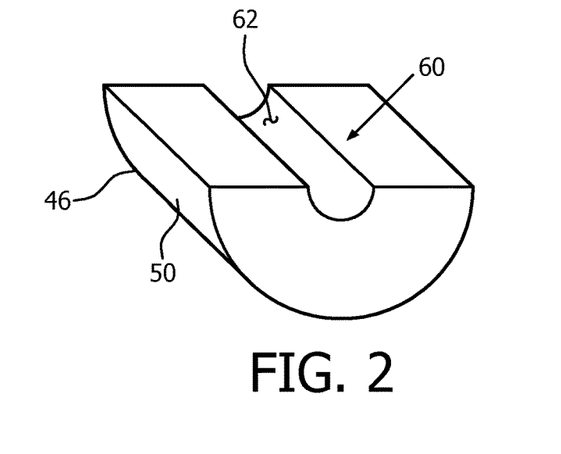
FIG. 2 is a cross-sectional view of one embodiment of the support member at least one porous portion.

At least one elongated support member 42 may have any cross-sectional shape, and, at least one conduit portion 44 and at least one porous portion 46 may each have different cross-sectional shapes. A generally circular and a generally rectangular cross-sectional shape are shown in FIGS. 2 and 4, respectively. As shown in FIG. 5, two strips of two different porous materials may be joined along the outer edges thereby creating an oval cross-sectional shape. In this exemplary embodiment, reinforcing material, i.e. a partial shell 95, may be disposed along the outer edges for protection.

Although FIG. 1 shows a single at least one conduit portion 44 and at least one porous portion 46, there may be more. For example, as stress may occur at the interface between mask 10 and at least one elongated support member 42, it may be desirable to have another conduit portion 44 adjacent mask 10. In an exemplary embodiment, there is a path of fluid communication from pressure generating system 16 to mask 10 via support assembly 40. As shown in FIG. 1, pressure generating system 16 is coupled to, and in fluid communication with, support assembly 40. More specifically, pressure generating system 16 is coupled to, and in fluid communication with, support member at least one conduit portion 44. Support member at least one conduit portion 44 is coupled to, and in fluid communication with, support member at least one porous portion 46. Support member at least one porous portion 46 is coupled to, and in fluid communication with, mask 10, and more specifically with mask opening 12. In this configuration, gas from pressure generating system 16 flows through support member at least one conduit portion 44 to support member at least one porous portion 46. Upon entering support member at least one porous portion 46, the gas flows axially via primary passage assembly 60 as well as radially. The portion of gas that flows axially via primary passage assembly 60 is communicated to mask 10.

Figure 11:
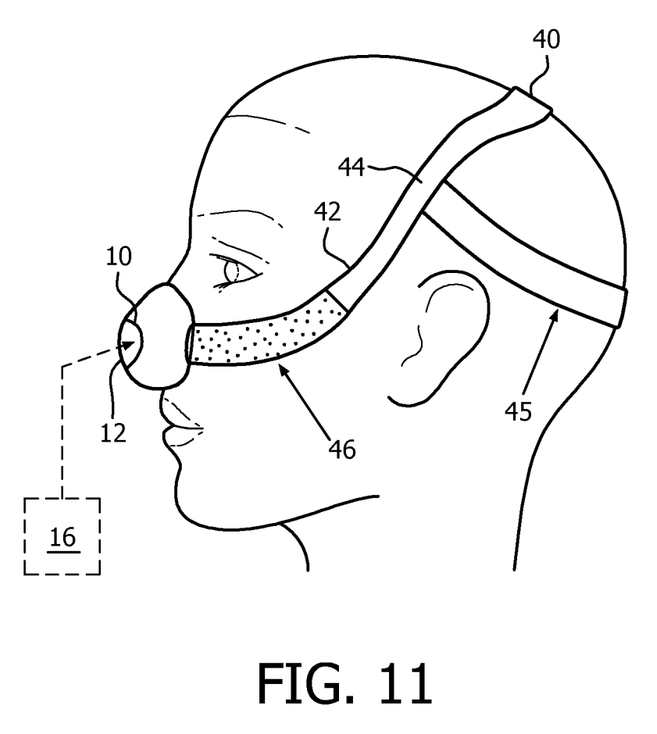
FIG. 11 is an isometric view of another embodiment of respiratory interface device.

In another exemplary embodiment, shown in FIG. 11, mask 10 is coupled to support assembly 40 and support assembly includes at least one elongated support member 42 having a strap portion 45 and at least one porous portion 46. Strap portion 45 is a strap without a conduit therein, and at least one porous portion 46 may be any of the embodiments described above. There is no pressure generating system 16, or, pressure generating system 16 does not directly communicate gas to support assembly 40. In this exemplary embodiment, support assembly 40 may be used to exhaust gas from mask 10. For example, mask 10 may be part of cold weather gear wherein atmospheric air is drawn in via mask opening 12, and an exhaled volume of gas exits mask 10 via support assembly 40. The exhaled volume of gas may be used to warm the user's cheeks or other body parts. In a similar exemplary embodiment, pressure generating system 16 is coupled by another conduit (shown schematically) to mask 10 and supplies gas to mask 10. As with the first embodiment in this paragraph, the user's exhaled volume of gas exits mask 10 via support assembly 40.

Figure 12:
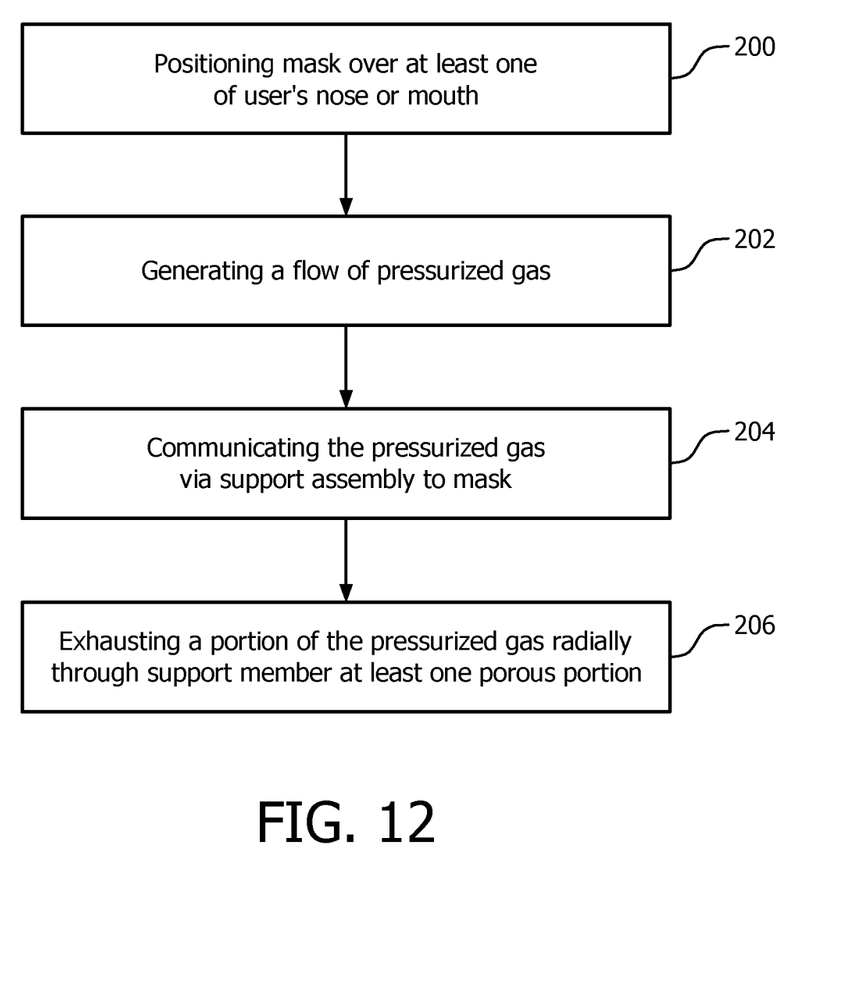
FIG. 12 is a flow chart of the steps of the method of using a respiratory interface device.

Accordingly, as shown in FIG. 12, respiratory interface device 8 may be used by performing the following steps: positioning 200 mask 10 over at least one of the user's nose or mouth, generating 202 a flow of pressurized gas, communicating 204 the pressurized gas via support assembly 40 to mask 10; and exhausting 206 a portion of the pressurized gas radially through support member at least one porous portion 46. It is noted that an exhaled volume of gas from the user creates pressure within mask 10. Thus, the step of generating 202 a flow of pressurized gas includes pressure generated by the user.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A support assembly for a respiratory interface device comprising: an elongated support member structured to contact a user, the support member having a conduit portion and at least one porous portion, wherein the conduit portion is structured to allow the passage of gas therethrough and adapted to be in fluid communication with a pressure generating system, and wherein the conduit portion is in fluid communication with the porous portion, wherein the porous portion is structured to allow for passage of gas therethrough and for exhaust of gas therefrom to an ambient environment, and wherein the porous portion is structured to be in fluid communication with a mask.

2. The support assembly of claim 1, wherein the porous portion is structured to have a selected axial flow rate and at least one radial exhaust rate.

3. The support assembly of claim 2, wherein:
the porous portion is a porous body;
the porous portion includes at least a first section and a second section; the first section having a first radial exhaust rate; and the second section having a second radial exhaust rate.

4. The support assembly of claim 3, wherein the first section and the second section extend coextensively along the porous portion.

5. The support assembly of claim 4, wherein: the first section is a tubular conduit having radial openings; the second section is a fabric cover; and the first section is substantially enclosed within the second section.

6. The support assembly of claim 3, wherein: the first section is a first body; the second section is a second body; and the first body and the second body are in fluid communication and disposed in series.

7. The support assembly of claim 2, wherein the porous portion is constructed from a material selected from the group including cell foam, woven material, fibrous textile, and a material having micro-passages.

8. The support assembly of claim 2, wherein the porous portion includes a primary passage assembly structured to provide a conduit for the axial passage of gas.

9. The support assembly of claim 8, wherein the primary passage assembly is a single passage.

10. The support assembly of claim 9, wherein the primary passage assembly single passage is generally circular in cross-section and has a first, greater radius at an upstream location and a second, lesser radius at a downstream location.

11. The support assembly of claim 2, wherein the porous portion includes a reinforcing assembly.

12. The support assembly of claim 11, wherein the reinforcing assembly includes at least one reinforcing element selected from the group including a rigid member, a stiff member, a shape maintaining member, a tension member, and a partial shell.

13. The support assembly of claim 11, wherein the reinforcing element is disposed within the support member.

14. The support assembly of claim 11, wherein the reinforcing element is disposed on the periphery of the support member.

15. The support assembly of claim 2, wherein: the porous portion includes a tubular conduit having radial openings and a fabric cover; and the tubular conduit is substantially enclosed within the fabric cover.

16. A support assembly for a respiratory interface device, the respiratory interface device including a mask having an opening, the support assembly comprising: an elongated support member structured to contact a user and including a porous portion, wherein the porous portion is structured to allow for axial passage of gas therethrough and radial exhaust of gas therefrom to an ambient environment; and wherein the porous portion being in fluid communication with the mask opening.

17. The support assembly of claim 16, wherein:
the porous portion is a porous body;
the porous portion is structured to have an axial flow rate and a radial exhaust rate;
the porous portion includes at least a first section and a second section;
the first section having a first radial exhaust rate; and the second section having a second radial exhaust rate.

18. The support assembly of claim 16, wherein the porous portion is constructed from a material selected from the group including cell foam, woven material, fibrous textile, and a material having micro-passages.

19. The support assembly of claim 16, wherein the porous portion includes a reinforcing assembly.

20. A method of using a respiratory interface device, the respiratory interface device including a mask having a mask opening therethrough and a pressure generating system structured to generate a flow of gas at an elevated pressure, a support assembly including at least one elongated support member structured to contact a user, the at least one support member having at least one conduit portion and a porous portion, the conduit portion is structured to allow the passage of gas therethrough, the conduit portion being in fluid communication with the pressure generating system and being in fluid communication with the porous portion, the porous portion is structured to allow for axial passage of gas therethrough and radial exhaust of gas therefrom to an ambient environment, and the porous portion being in fluid communication with the mask opening, the method comprising: positioning the mask over at least one of the user's nose or mouth; generating a flow of pressurized gas; communicating the pressurized gas via the support assembly to the mask; and exhausting a portion of the pressurized gas radially through the porous portion.

* * * * *